(12) United States Patent
Hopkins (10) Patent No.: US 8,914,245 B2
(45) Date of Patent: Dec. 16, 2014

(54) ULTRASOUND PROBE WITH ACCELEROMETER

(76) Inventor: Andrew David Hopkins, Sutton Coldfield (GB)

( * ) Notice: Subject to any disclaimer, the term of this patent is extended or adjusted under 35 U.S.C. 154(b) by 318 days.

(21) Appl. No.: 13/256,763

(22) PCT Filed: Mar. 22, 2010

(86) PCT No.: PCT/GB2010/050480
§ 371 (c)(1),
(2), (4) Date: Sep. 15, 2011

(87) PCT Pub. No.: WO2010/106379
PCT Pub. Date: Sep. 23, 2010

(65) Prior Publication Data
US 2011/0320143 A1    Dec. 29, 2011

Related U.S. Application Data

(60) Provisional application No. 61/161,910, filed on Mar. 20, 2009.

(51) Int. Cl.
| | |
|---|---|
| *G01F 17/00* | (2006.01) |
| *A61B 8/00* | (2006.01) |
| *A61B 8/08* | (2006.01) |
| *A61B 8/12* | (2006.01) |
| *G10K 11/35* | (2006.01) |
| *G01P 7/00* | (2006.01) |
| *G01S 15/89* | (2006.01) |

(52) U.S. Cl.
CPC ............... *A61B 8/12* (2013.01); *A61B 8/4254* (2013.01); *A61B 8/483* (2013.01); *G10K 11/35* (2013.01); *A61B 2562/0219* (2013.01); *G01P 7/00* (2013.01); *G01S 15/8936* (2013.01)
USPC .............................. 702/56; 600/300; 600/101

(58) Field of Classification Search
USPC .......................................................... 702/56
See application file for complete search history.

(56) References Cited

U.S. PATENT DOCUMENTS

| | | | | |
|---|---|---|---|---|
| 3,572,899 A | * | 3/1971 | Bell, Jr. ........................ | 359/311 |
| 4,170,142 A | * | 10/1979 | Posakony et al. ............... | 73/603 |
| 5,095,752 A | * | 3/1992 | Suzuki et al. ............... | 73/514.32 |
| 5,130,937 A | * | 7/1992 | Kumar et al. ................. | 702/141 |
| 5,538,004 A | * | 7/1996 | Bamber ....................... | 600/443 |

(Continued)

FOREIGN PATENT DOCUMENTS

EP    1348385 A1    10/2003

OTHER PUBLICATIONS

The International Search Report dated Jun. 23, 2010.

*Primary Examiner* — Jonathan C Teixeira Moffat
*Assistant Examiner* — Alvaro Fortich (57) ABSTRACT

An ultrasonic probe (10) that scans a subject with beams of high frequency sound. The probe (10) includes a transducer (26) to produce high frequency sound waves, a means to steer the sound waves in the proper direction, a printed circuit board (22) with a non-volatile memory (38), a micro electrico-mechanical accelerometer integrated circuit (32) and an outlet connector (19). The accelerometer (32) is configured to detect the movement of the probe (10) in from two to three axes when the probe (10) is rotated or moved in a linear direction to allow the probe (10) to detect images from more than one plane.

20 Claims, 8 Drawing Sheets

(56) References Cited

U.S. PATENT DOCUMENTS

| | | | |
|---|---|---|---|
| 5,582,173 A * | 12/1996 | Li | 600/443 |
| 6,122,538 A | 9/2000 | Sliwa, Jr. | |
| 6,142,947 A * | 11/2000 | Tran et al. | 600/459 |
| 6,150,947 A * | 11/2000 | Shima | 340/692 |
| 6,171,248 B1 * | 1/2001 | Hossack et al. | 600/459 |
| 6,338,716 B1 | 1/2002 | Hossack et al. | |
| 6,371,903 B1 * | 4/2002 | Blanc et al. | 600/2 |
| 7,066,887 B2 * | 6/2006 | Flesch et al. | 600/447 |
| 7,443,154 B1 * | 10/2008 | Merewether et al. | 324/67 |
| 8,366,622 B2 * | 2/2013 | Slayton et al. | 600/439 |
| 2001/0051766 A1 * | 12/2001 | Gazdzinski | 600/309 |
| 2003/0176787 A1 * | 9/2003 | Gilbert et al. | 600/437 |
| 2004/0264707 A1 * | 12/2004 | Yang et al. | 381/77 |
| 2005/0193820 A1 * | 9/2005 | Sheljaskow et al. | 73/649 |
| 2006/0058676 A1 * | 3/2006 | Yagi et al. | 600/459 |
| 2006/0235316 A1 * | 10/2006 | Ungless et al. | 600/509 |
| 2007/0010742 A1 * | 1/2007 | Torp et al. | 600/437 |
| 2007/0010747 A1 * | 1/2007 | Sabourin et al. | 600/453 |
| 2007/0135807 A1 * | 6/2007 | Knodel et al. | 606/17 |
| 2008/0004528 A1 * | 1/2008 | Fitzsimons et al. | 600/439 |
| 2008/0146932 A1 | 6/2008 | Chalana et al. | |
| 2008/0146941 A1 | 6/2008 | Dala-Krishna | |
| 2008/0194951 A1 * | 8/2008 | Poland | 600/437 |
| 2008/0200807 A1 * | 8/2008 | Wright et al. | 600/443 |
| 2008/0249418 A1 * | 10/2008 | Shikata et al. | 600/459 |
| 2009/0112089 A1 * | 4/2009 | Barnard et al. | 600/443 |
| 2009/0130642 A1 * | 5/2009 | Tada et al. | 434/262 |
| 2009/0209860 A1 * | 8/2009 | Hasegawa et al. | 600/445 |
| 2009/0264754 A1 * | 10/2009 | Dahl et al. | 600/438 |
| 2009/0306509 A1 * | 12/2009 | Pedersen et al. | 600/446 |
| 2010/0194692 A1 * | 8/2010 | Orr et al. | 345/173 |
| 2010/0201573 A1 * | 8/2010 | Lamming | 342/451 |
| 2011/0034806 A1 * | 2/2011 | Hartov et al. | 600/443 |
| 2011/0248603 A1 * | 10/2011 | Tezuka et al. | 310/314 |
| 2012/0238875 A1 * | 9/2012 | Savitsky et al. | 600/443 |

* cited by examiner

ULTRASOUND PROBE WITH ACCELEROMETER

CROSS-REFERENCE TO RELATED APPLICATION

This application is the 35 U.S.C. §371 national stage of PCT Application No. PCT/GB10/050480, international filing date 22 Mar. 2010, which claims priority to U.S. Provisional Application No. 61/161,910, filed on 20 Mar. 2009, both of which are incorporated herein by reference in their entireties.

FIELD OF THE INVENTION

This application is a European application that claims priority to co-pending U.S. Provisional Patent Application entitled, "Ultrasound Probe with Accelerometer", having Ser. No. 61/161,910, filed Mar. 20, 2009, which are entirely incorporated herein by reference.

This present invention discloses an ultrasound probe with accelerometer for scanning the outside or inside of the human body for producing visual images of various organs in the body.

SUMMARY OF THE INVENTION

Handheld ultrasonic probes attached by a cable to a processing unit and a display unit are known in the field. This invention incorporates an accelerometer in the probe to detect movement of the probe in three axes as the probe is rotated or moved in a linear direction. The accelerometer detects the rotation of the probe along the longitudinal axes of the probe. This allows the projection of images of the reflected ultrasound waves from different angles. Images can be produced from the transverse plane and the sagittal plane. 3D images can be produced.

The probe may have an electric motor to mechanically move the sound beam or it can have a number of transducer elements, such as piezoelectric crystals, which may arranged in an array to steer the sound beam. Either of these means can be used to steer the sound beam in the proper direction.

The conventional ultrasonic probe has a fluid bulb at its forward end. By producing a probe that is cylindrical and of a uniform diameter, the probe can be used for transrectal, pelvic floor and urethra scanning.

This invention uses a three-axis digital accelerometer suitable with use with probe of this invention.

The accelerometers used with the probe of this invention can be a low cost analog devices. The LIS3LV02DL accelerometer made by STMicroelectronics is preferred type of accelerometer because it has a programmable interrupt output when it detects movement. With this feature the processor does not have to waste time if there is nothing to see. A three-axes digital accelerometer is preferred over a two-axes accelerometer.

PARTS LIST

| | |
|---|---|
| 10. | Ultrasound Probe |
| 12. | Probe Switch |
| 14. | Orientation spot |
| 16. | Soft grips |
| 17. | Longitudinal axis |
| 18. | Fluid chamber |
| 19. | Outlet connector |
| 20. | Probe casing |
| 22. | Interface Printed circuit board |
| 24. | Motor |
| 26. | Transducer |
| 28. | Transducer cradle |
| 30. | Scanner connector |
| 32. | Micro electro-mechanical systems accelerometer integrated circuit (MEMS) |
| 34. | Logic buffers |
| 36. | Probe switch connector |
| | Non-volatile memory |
| | Transverse plane of bladder |
| 42 | Sagittal plane of bladder |

DETAILED DESCRIPTION OF THE PREFERRED EMBODIMENT

Ultrasound probes normally consist of a piezoelectric element which is driven by a high voltage pulse to produce a high frequency sound wave between 1-20 MHz. The piezoelectric element may consist of a number of elements as used in a phased array or electronic probe or a single or annular element mechanically driven.

Figure 1:
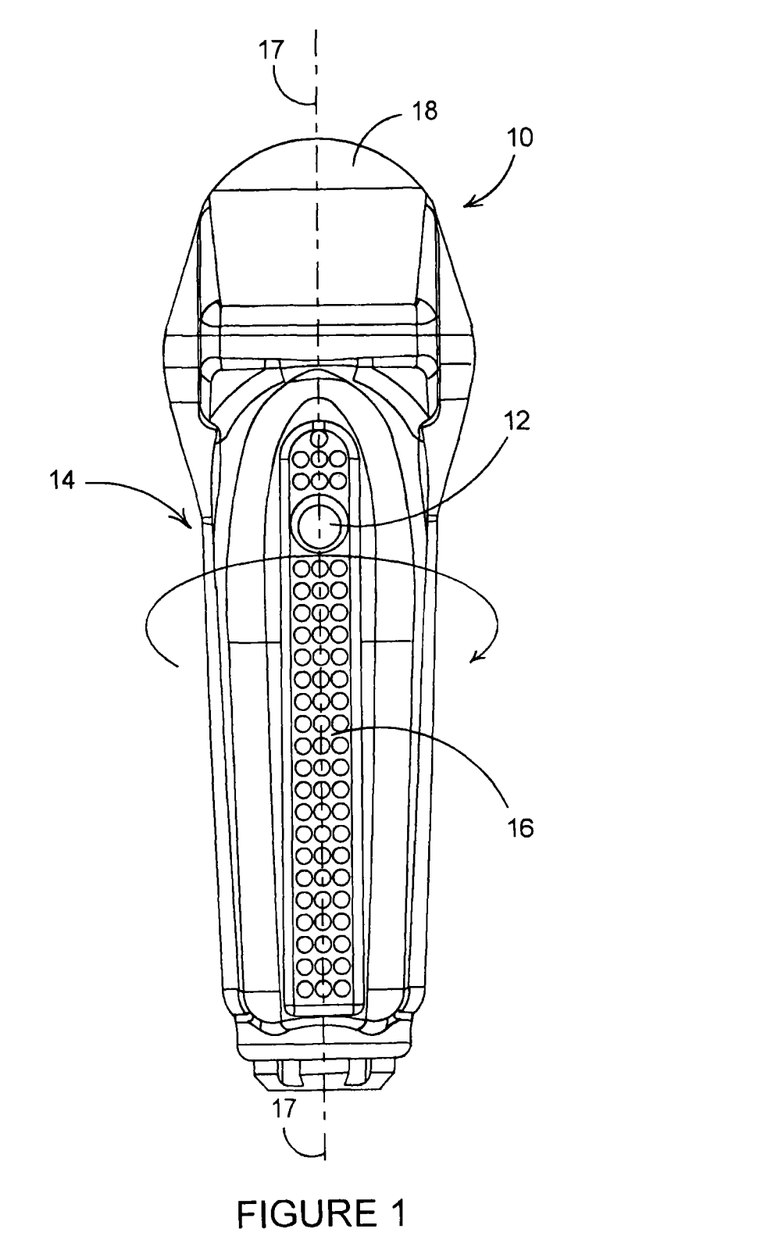
FIG. 1 is the front longitudinal view of the ultrasound probe with accelerometer of this invention.
Figure 2:
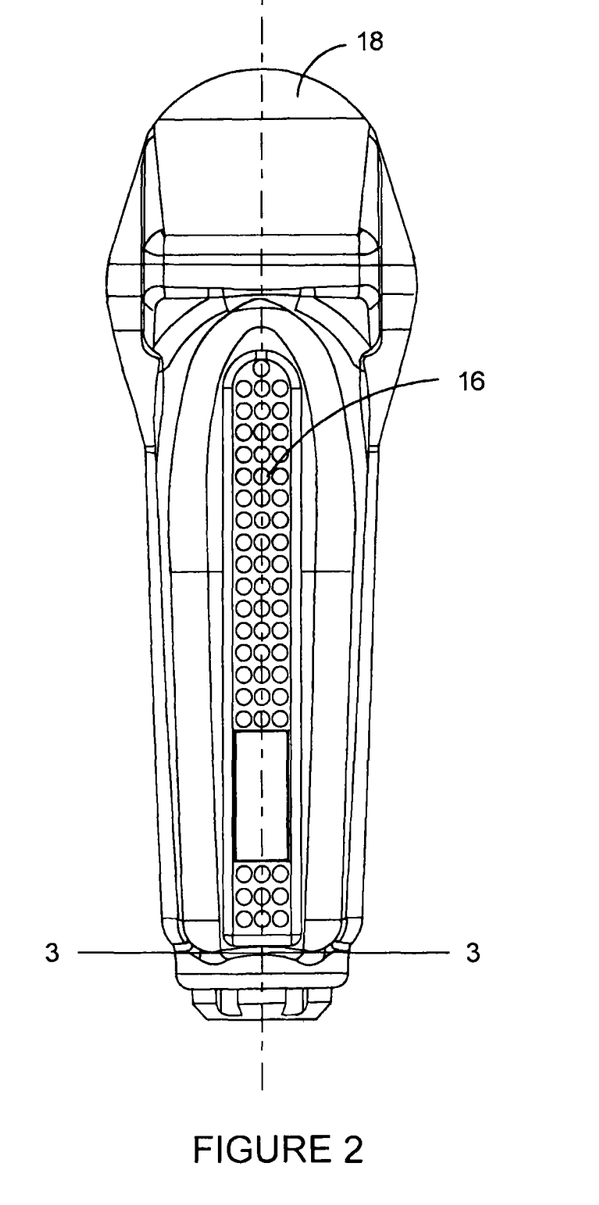
FIG. 2 is the back longitudinal view of the ultrasound probe of FIG. 1.
Figure 3:
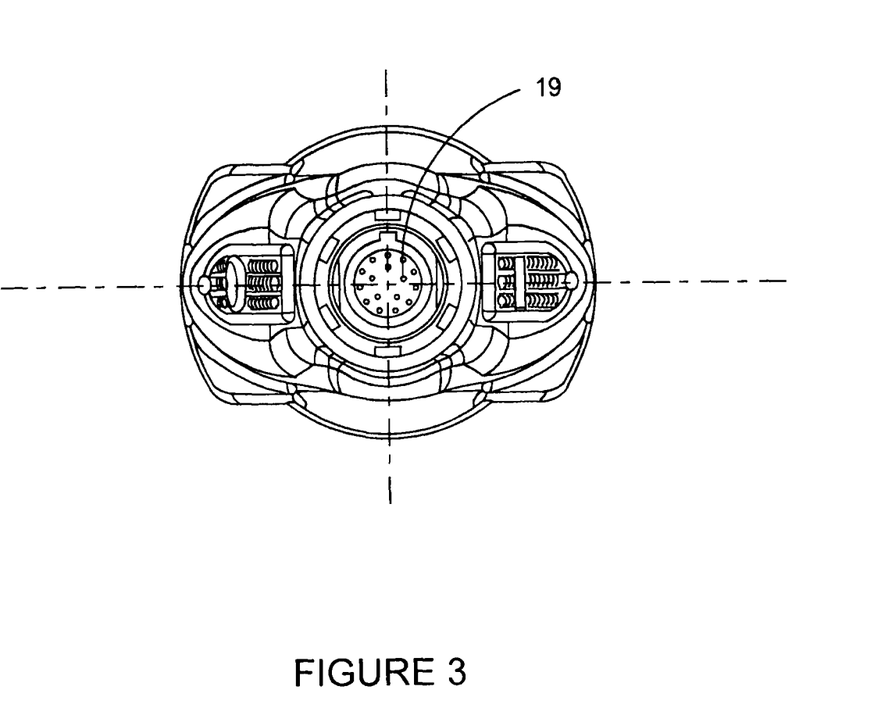
FIG. 3 is the bottom end view of the ultrasound probe of FIG. 1.

FIG. 1 illustrates a front longitudinal view of the ultrasound probe with accelerometer 10 of this invention. This ultrasound probe with accelerometer 10 as shown in the longitudinal cross-section of FIG. 4 consists of the piezoelectric element in a transducer 26, electric drive motor 24, interface printed circuit board (PCB 22, probe switch 12 and outlet connector (19).

Figure 4:
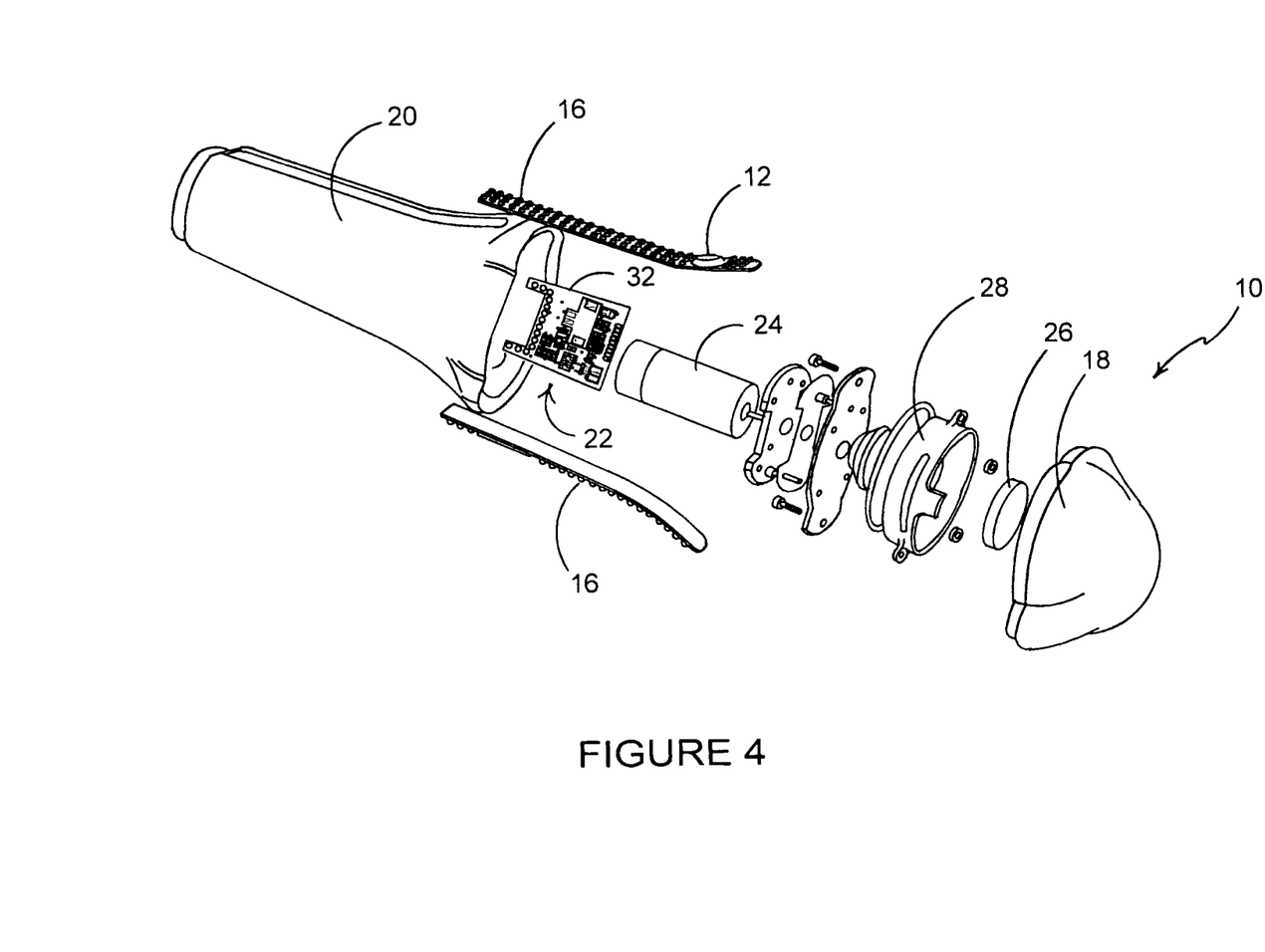
FIG. 4 a longitudinal cross-section of the internal components of the ultrasound probe of FIG. 1.

The transducer 26 is a piezoelectric transducer which converts mechanical waves to electrical signals and vice versa. These transducers frequently incorporate a polycrystalline piezoelectric and may be based upon the composition $Pb(Zr_{1-x},Ti_x)O_3$, generally known as PZT. Other crystals which convert mechanical waves to electrical signals may also be used.

Figure 5:
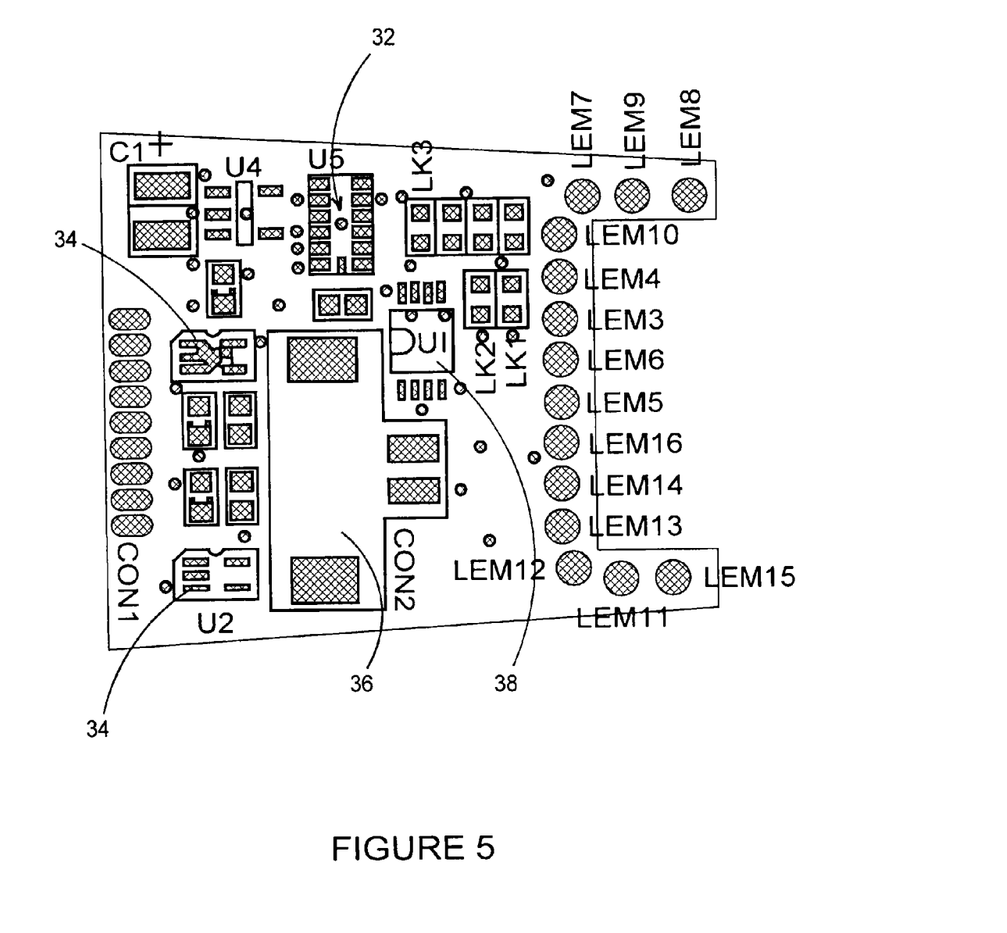
FIG. 5 is a schematic view of the Micro electro-mechanical systems accelerometer integrated circuit(MEMS)

The printed circuit board 22 shown in FIG. 5 acts as the interface between the incoming cable from the ultrasound scanner electronic and the probe element.

The printed circuit board 22 contains the interface electronics containing the non-volatile memory 38, the micro electro-mechanical systems accelerometer integrated circuit (MEMS) 32, and clock buffers. An accelerometer is a device that measures non-gravitational accelerometers. The accelerometer is detected by mechanically accelerating the accelerometer via its casing.

MEMS Physical Principles

Under the influence of external accelerometers that are transmitted via the casing the MEMS sensor deflects from its neutral position. This deflection is measured in an analog or digital manner. Most commonly the capacitance between a set of fixed beams and a set of beams attached to the proof mass is measured. This method is simple, reliable and does not require additional process steps making it inexpensive.

An accelerometer measures the non gravitational acceleration it experiences. It is simplest to consider that the gravitational forces accelerate the whole accelerometer equally, and therefore give no reading. Non-gravitational acceleration is produced by forces other than gravity or inertial forces. Such forces include all simple mechanical forces. These are transmitted to the accelerometer device through mechanical stress on its mounting.

The non-volatile memory 38 can be used to contain the serial number, probe characteristics, time gain characteristics, last used settings for when probe is interchanged with other types of probe, i.e. abdominal, endocavity, linear etc.

The accelerometer detects movement of the probe in three axes and allows detection of the probe 10 when rotated or moved in a linear direction. The probe 10 could be used to detect movement of the probe in two axes, but the results would be less accurate.

90 Degree Scanning

Figure 6:
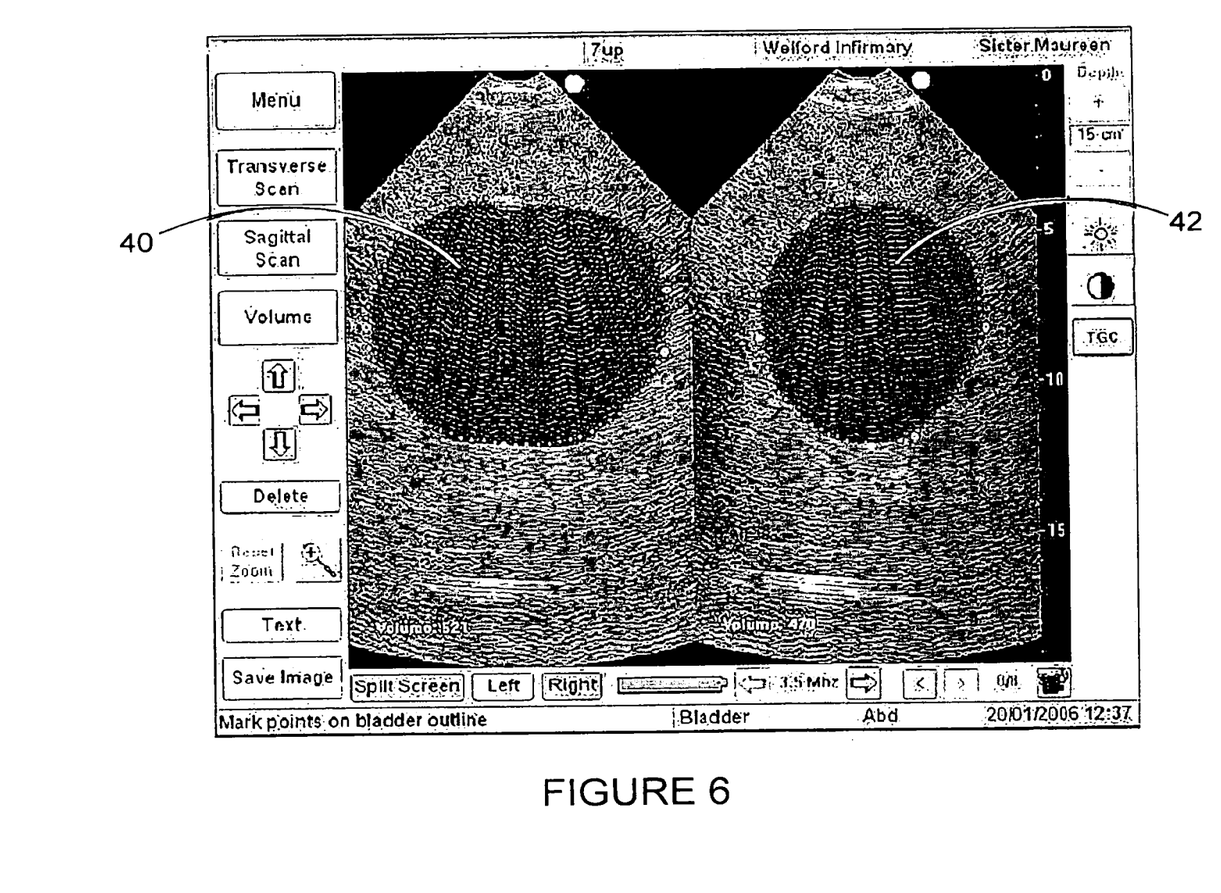
FIG. 6 is side-by-side view taken at right angles to each other of a human bladder (Transverse and Sagittal planes)

When scanning an organ (such as a bladder) as shown in FIG. 6 and the probe 10 is aligned in the normal direction for scanning that organ and the probe switch 12 is then pressed, it will save the image from that position and mark that position as 0 degrees. The probe 10 is then rotated through 90 degrees as shown in the sketch below. When the 90 degree position is detected by the sensor, the information can be automatically saved or used to open a second window to display the sagittal view, which is the vertical plane passing through the standing body from front to back. The two views can also be used to calculate the organ volume (such as bladder volume) to a greater accuracy.

180 Degree Scanning

If the probe is rotated through 180 degrees, a complete 3D image of the organ will be obtained to allow greater accuracy in determining dimensions and volume.

Linear Scanning

If the probe is moved linearly across the organ a 3D image of the organ could be obtained. The velocity is the integral of the acceleration measured by the MEMS accelerometer 32 and the distance traveled is the integral of the velocity. The linear displacement is interpolated from the accelerometer and deceleration and time of displacement of the probe 10.

Bladder Scanning

The image shown in FIG. 6 are two scans taken at right angles to each other of the bladder of a person (Transverse and Sagittal planes).By using both images a more accurate valuation of the bladder volume can be made. By using the MEMS accelerometer 32 sensor the 90° turn in the probe 10 can be detected and the image automatically switched to the other window. This allows the two images to be shown side by side.

Single Plane Scanning

The scan can be started by either pressing the probe switch 12 on the probe 10 or on the START button on the monitor screen as shown in FIG. 6, the maximum bladder size can be manually or automatically detected.

Manual Detection

Manual detection is achieved by the operator moving the probe 10 to visually maximize the image of the bladder. The operator places the probe 10 approximately over where the bladder should be and then moves the probe in the horizontal or vertical direction to centre the bladder, then moves the probe angularly with the front end of the probe as represented by the fluid chamber 18 remaining in the same position until the maximum bladder area is observed. When the operator finds the maximum bladder area, the operator presses the probe switch 12 or the STOP/Freeze button on the monitor screen to stop the scan and save the image and instigate the calculation for the bladder volume.

Automatic Detection

Automatic detection is achieved by the operator moving the probe 10 as described in the manual detection. During the scan each frame is compared to see if the image of the bladder area is larger than that in the preceding frame. The frame with the image of the largest bladder area is then stored.

Pressing the probe switch 12 or the Stop/freeze button on the monitor screen to stop the scan would instigate the calculation for the bladder volume using the frame image stored with the image of the bladder with the maximum area obtained during the investigation.

Orientation Spot

The probe 10 of this invention has an orientation spot 14 as shown FIG. 1 which provides the operator with a starting point analogous to a GPS starting point or on a map direction website on the internet.

Transverse and Sagittal Plane Scanning

Pressing the probe switch 12 or the START button on the monitor screen starts the transverse scan, so that the maximum bladder size can be detected either manually as described previously or automatically. Automatic detection is achieved by moving the probe 10 to maximize the image of the bladder; each frame is compared to see if the image of the bladder area is larger than that in the preceding frame. The frame with the image of the largest bladder area is then stored.

After having obtained the transverse scan, the sagittal scan can then be obtained manually when the operator rotates the probe 90° to the previous scan and repeats the process of scanning as just denote the sagittal scan position and another orientation spot or dot 14 or the start/stop button on the monitor denoting the transverse position. The operator moves the probe 10 to visually maximize the image of the bladder. Pressing the probe switch or the Stop/Freeze button on the screen will stop the scan and save the image and instigate the calculation for the bladder volume. However, it could also instigate the calculation for the bladder volume using the transverse and sagittal frame images stored showing the bladder with the maximum area.

The sagittal scan can also be obtained automatically such that when the operator rotates the probe 10 by 90°. The MEMS 32 accelerometer sensor automatically senses when the probe 10 is rotated 90° to automatically display the sagittal plane on the display either individually or side by side with the transverse scan.

As the operator moves the probe 10 to visually maximize the image of the bladder the frame with the image of the largest bladder area is then stored. Pressing the probe switch 12 or the STOP/Freeze button on the screen to stop the scan will start the calculation for the bladder volume using the images stored with the bladder with the maximum area for transverse and sagittal frames. This method can also apply to other organs such as the prostate.

Figure 7A:
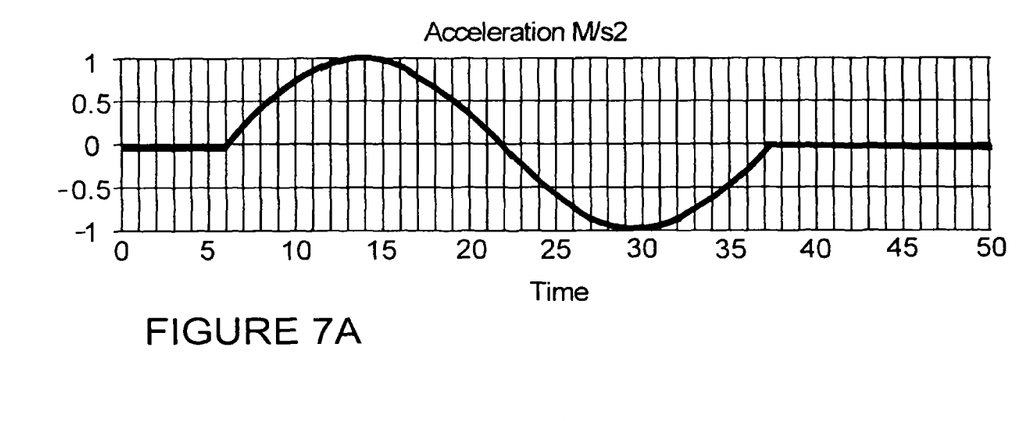
FIG. 7A is a graph showing a measurement of the accelerometer graphically displaying velocity and distance traveled which shows that velocity is the integral of accelerometer.

The non-contact method to measure accelerometer, velocity, and distance traveled is illustrated in FIG. 7A. Velocity is the integral of Accelerometer observed. When the operator finds the maximum bladder area, the operator presses the probe button or the STOP/Freeze button on the screen to stop the scan and save the image and instigate the calculation for the bladder volume.

Automatic Detection

Automatic detection is achieved by the operator moving the probe as described in the manual detection. During the scan each frame is compared to see if the image of the bladder area is larger than that in the preceding frame. The frame with the image of the largest bladder area is then stored.

Pressing the probe button or the Stop/freeze button on the screen to stop the scan would instigate the calculation for the bladder volume using the frame image stored with the image of the bladder with the maximum area obtained during the investigation.

ORIENTATION

The orientation of the probe 10 can be determined by placing an orientation spot or dot 14 as illustrated in FIG. 1 and in the sketch below. It is analogous to the start position of GPS or map directions on some internet websites such as Mapquest™.

Transverse and sagittal Plane Scanning

Pressing the probe switch 12 or the START button on the monitor screen starts the transverse scan so that the maximum bladder size can be detected either manually as described previously or automatically. Automatic detection is achieved by moving the probe 10 to maximize the image of the bladder, each frame is compared to see if the image of the bladder area is larger than that in the preceding frame. The frame with the image of the largest bladder area is then stored. After having obtained the transverse scan, the sagittal scan can then be obtained manually when the operator rotates the probe 90° to the previous scan and repeats the process of scanning as just described for the transverse scan. The probe 10 is usually marked with a spot or dot on the probe to denote the sagittal scan position and another orientation spot or dot 14 or the start/stop button on the monitor denoting the transverse position. The operator moves the probe 10 to visually maximize the image of the bladder. Pressing the probe switch or the Stop/Freeze button on the screen will stop the scan and save the image and instigate the calculation for the bladder volume. However, it could also instigate the calculation for the bladder volume using the transverse and sagittal frame images stored showing the bladder with the maximum area.

The sagittal scan can also be obtained automatically such that when the operator rotates the probe 10 by 90°. The MEMS 32 accelerometer sensor automatically senses when the probe 10 is rotated 90° to automatically display the sagittal plane on the display either individually or side by side with the transverse scan. As the operator moves the probe 10 to visually maximize the image of the bladder the frame with the image of the largest bladder area is then stored. Pressing the probe switch 12 or the STOP/Freeze button on the screen to stop the scan will start the calculation for the bladder volume using the images stored with the bladder with the maximum area for transverse and sagittal frames. This method can also apply to other organs such as the prostate. The non-contact method to measure accelerometer, velocity, and distance traveled is illustrated in FIG. 7A.

Figure 7B:
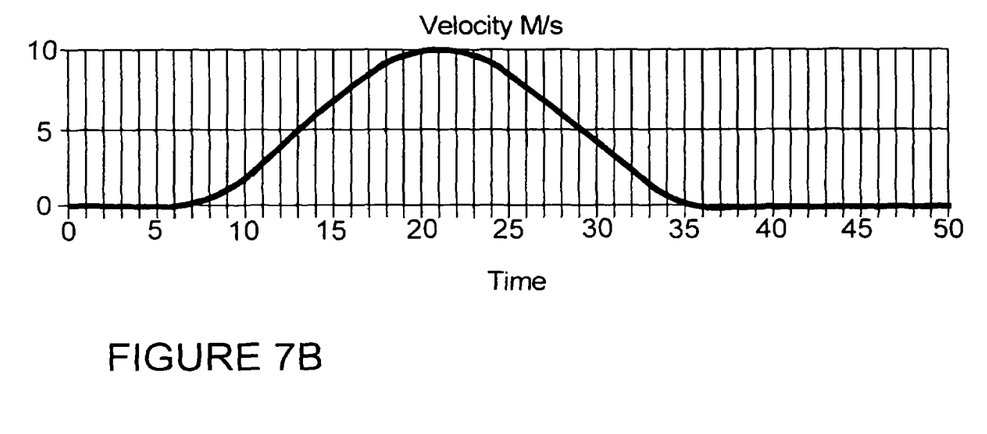
FIG. 7B is a graph showing that distance traveled in the integral of velocity (double integral of accelerometer).

Velocity is the integral of Accelerometer as shown in FIG. 7B. The distance is the integral of velocity (double integral of accelerometer.

Different Approaches to Accelerometer Sensing

Piezo-film (Vibration, shock), AC Response only, Senses many things besides motion (sound, temperature, pressure)

Electromechanical Servo (Tilt, Inertial) DC accurate, low frequency only.

Piezoelectric (Vibration, Shock) Wide-dynamic range, AC Response only.

Figure 8A:
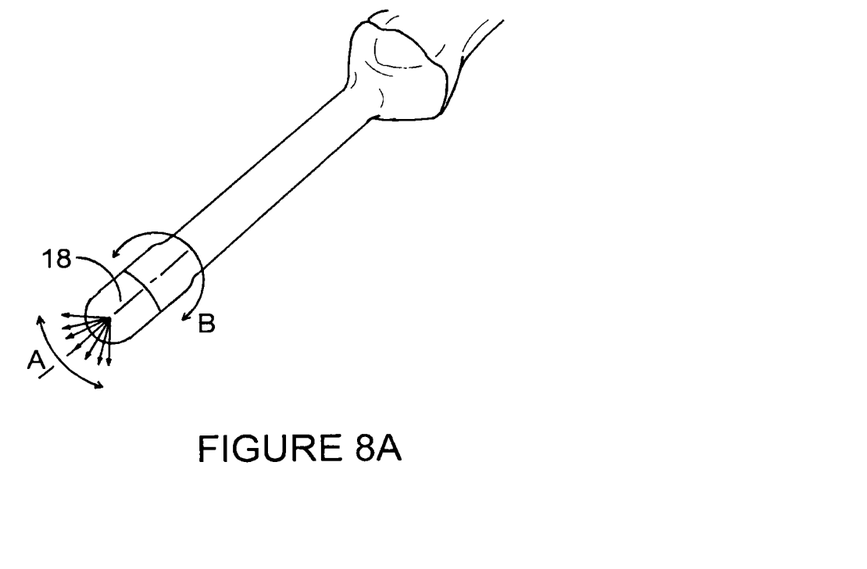
FIG. 8A is a longitudinal view of an end cavity ultrasound probe with accelerometer.
Figure 8B:
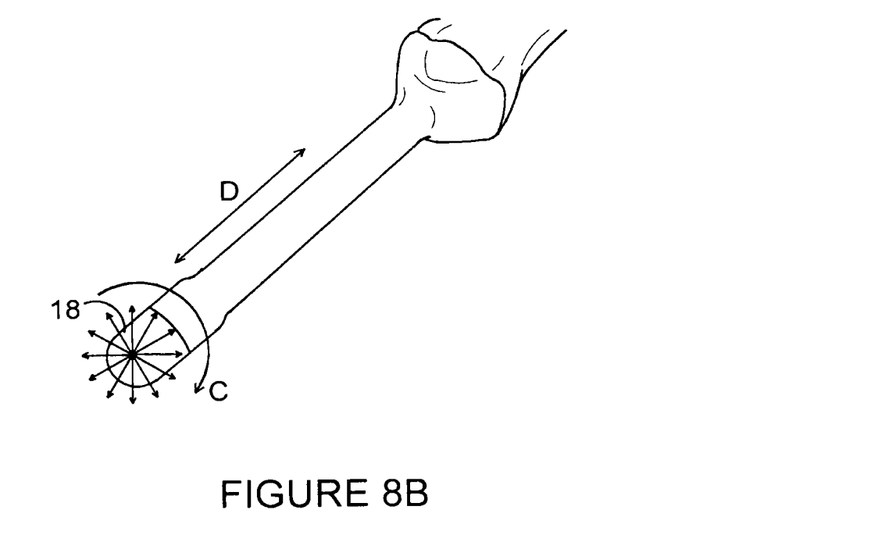
FIG. 8B is longitudinal view of a sidefire ultrasound probe with accelerometer.

Liquid tilt sensors (Tilt) DC response,

Bulk Micromachined Piezo Resistive (Tilt, Vibration, Inertial) DC Response,

Bulk Micromachined Capacitive (Tilt, Vibration, and Inertial) DC Response, Good DC accuracy, low noise, Surface Micro machined Capacitive (Tilt, Vibration, and Inertial) DC Response, Standard IC form factors Endocavity Probes Endocavity probes as illustrated in FIGS. 8A and 8B are used for transrectal, pelvic floor and urethra scanning.

In a similar mode to the abdominal probe scan of the bladder the prostate is usually scanned in the anteroposterior and sagittal planes and as described before for the abdominal probe, the 90° turn can be automatically detected using the MEMS 32 accelerometer sensor and the image automatically saved. Using an endfire endocavity probe as illustrated in FIG. 8A an arc of sound is emitted in line with the shaft of the probe (A) (in the directions indicated by the arrows), for example to scan a prostate situated in front of the probe. If the probe is rotated through 180° (B) whilst scanning in this mode, then by using a MEMS 32 accelerometer sensor in the probe to sense the angular rotation, a 3D image can be built up.

Using a sidefire endocavity probe as the sound is emitted at right angles to the shaft of the probe (C) to image the tissue surrounding the probe. To image the rectum for example, extracting the probe in a linear mode (D) whilst scanning, a 3D image can be built up. The MEMS 32 accelerometer sensor is used to sense the linear motion. Although the sensor only detects the accelerometer, the linear displacement is interpolated from the accelerometer and deceleration and time of displacement of the probe.

The above applies to both mechanical and electronic Endocavity probes. Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

Therefore, having thus described the disclosure, at least the following is claimed:

1. An ultrasonic probe which scans a subject with beams of sound waves comprising:
   a transducer to produce sound waves;
   a means to steer the sound waves in the direction of a subject;
   a printed circuit board with a non-volatile memory;
   a micro electrico-mechanical accelerometer integrated circuit;
   an outlet connector; and
   a logic device that is electrically coupled to the accelerometer and transducer,
   wherin said micro electrico-mechanical accelerometer integrated circuit detects the movement of the probe in two to three axes when the probe is rotated or moved in a linear direction to allow the probe to detect images from more than one plane, wherein the logic device instructs the transducer to produce the sound waves for scanning the subject and saves a first image from a first position based on the movement detection of the micro electrico-mechanical accelerometer integrated circuit, wherein the logic determines that the ultrasonic probe is rotated to a second predetermined position relative to the first position based on the movement detection of the micro electrico-mechanical accelerometer integrated circuit, and responsive to determining that the ultrasonic probe is rotated the second predetermined position, the logic device instruct the transducer to produce the sound waves for scanning the subject and saves a second image from the second predetermined position.

2. The probe of claim 1 in which the probe can produce a 3d image of an organ of a subject when the probe is rotated 180 degrees.

3. The probe of claim 1 in which the probe can produce a 3d transverse plane scanning of an organ of a subject and sagittal plane scanning by linearly moving the probe across the body.

4. An ultrasonic endocavity probe which scans a cavity of a subject having an end for inserting into the cavity comprising:
- a transducer to produce sound waves;
- a means to steer the sound waves in the direction of a subject;
- a printed circuit board with a non-volatile memory;
- a micro electrico-mechanical accelerometer integrated circuit;
- an outlet connector; and
- a logic device that is electrically coupled to the accelerometer and transducer, said micro electrico mechanical accelerometer integrated circuit detects the movement of the probe in two or three axes when the probe is rotated or moved in a linear direction to allow the probe to detect images from more than one plane, said probe being of a size and shape to enter the cavity of the subject, wherein the logic device instructs the transducer to produce the sound waves for scanning the subject and saves a first imagine from a first position based on the movement detection of the micro electrico mechanical accelerometer integrated circuit, wherein the logic device determines that the ultrasonic probe is rotated to a second predetermined position relative to the first position based on the movement detection of the micro electrico-mechanical accelerometer integrated circuit, and responsive to determining that the ultrasonic probe is rotated the second predetermined position, the logic device instructs the transducer to produce the sound waves for scanning the subject and saves a second image from the second predetermined position.

5. The probe of claim 4 in which probe emits an arc of sound forward (endfire) of the probe.

6. The probe of claim 4 in which the probe emits an arc of sound at right angles (sidefire) to the longitudinal axes of the probe.

7. The probe of claim 4 which also has clock buffers.

8. The probe of claim 4 which has piezoelectric crystals in the transducer.

9. An ultrasound imaging system comprising a hand held ultrasonic probe which scans a subject with beams of sound waves comprising:
- a transducer with a piezoelectric crystals to produce sound waves;
- a means to steer the sound waves in the direction of a subject;
- a printed circuit board with a non-volatile memory;
- a micro electrico-mechanical accelerometer integrated circuit;
- an outlet connector;

said micro electrico-mechanical accelerometer integrated circuit detects the movement of the probe in two or three axes when the probe is rotated or moved in a linear direction to allow the probe to detect images from more than one plane and a console processing and display unit coupled by a cable to the hand-held display, in which the piezoelectric crystals convert the ultrasonic reflected energy from the subject into electrical signals transferred from the probe over the cable to the processing unit, wherein the processing unit instructs the transducer to produce the sound waves for scanning the subject and saves a first image from a first position based on the movement detection of the micro electrico-mechanical accelerometer integrated circuit, wherein the processing unit determines that the ultrasonic probe is rotated to a second predetermined position relative to the first position based on the movement detection of the micro electrico-mechanical accelerometer integrated circuit, and responsive to determining that the ultrasonic probe is rotated the second predetermined position, the processing unit instructs the transducer to produce the sound waves for scanning the subject and saves a second image from the second predetermined position.

10. An ultrasonic probe which scans a subject with beams of sound waves comprising:
- a transducer to produce sound waves;
- means to steer the sound waves in the direction of a subject;
- a printed circuit board with a non-volatile memory,
- a micro electric-mechanical accelerometer integrated circuit,
- an outlet connector; and
- a logic device that is electrically coupled to the accelerometer and transducer, wherein said micro electric-mechanical accelerometer integrated circuit detects the movement of the probe in all three axes when the probe is rotated or moved in a linear direction to allow the probe to detect images from more than one plane, wherein the logic device instructs the transducer to produce the sound waves for scanning the subject and saves a first image from a first position based on the movement detection of the micro electric-mechanical accelerometer integrated circuit, wherein the logic device determines that the ultrasonic probe is rotated to a second predetermined position relative to the first position based on the movement detection of the micro electric-mechanical accelerometer intergrated circuit, and responsive to determining that the ultrasonic probe is rotated the second predetermined position, the logic device instructs the tranducer to produce the sound waves for scanning the subject and saves a second image from the second predetermined position.

11. The probe of claim 10 in which the accelerometer is a digital 3 axis device.

12. The probe of claim 10 in which the accelerometer has an interrupt output sensor when it detects movement to prevent the processor to which the probe is attached from wasting time looking at images when the images produced are not clear views of an organ of a subject.

13. The probe of claim 12 in which the means to steer the sound waves is an electric motor to mechanically move the sound direction.

14. The probe of claim 12 in which the sound waves are produced by a plurality of transducer elements, including a piezoelectric crystal array, with the means to steer the sound waves arranged in the array.

15. The probe of claim 12 in which the sound waves are steered by an electric motor.

16. The probe of claim 15 which is connected to a video monitor with controls.

17. The probe of claim 1 in which the means to steer the sound waves is an electric motor to mechanically move the sound direction.

18. The probe of claim 1 in which the sound waves are produced by at least one transduce element, including a piezoelectric crystal array, with the means to steer the sound waves arranged in the array.

19. The probe of claim 1 in which the sound waves are steered by an electric motor.

20. The probe of claim 1 which is connected to a video monitor with controls.

* * * * *